(12) United States Patent
Humphries et al.

(10) Patent No.: US 10,113,977 B2
(45) Date of Patent: *Oct. 30, 2018

(54) APPARATUS AND METHOD FOR ACQUIRING A TWO-DIMENSIONAL IMAGE OF THE SURFACE OF A THREE-DIMENSIONAL OBJECT

(71) Applicant: Capsugel Belgium NV, Bornem (BE)

(72) Inventors: Mark Robson Humphries, Saffron Walden (GB); Paul Antony Merritt, Royston (GB); Stefaan Jaak Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/413,134

(22) Filed: Jan. 23, 2017

(65) Prior Publication Data

US 2017/0131221 A1     May 11, 2017

Related U.S. Application Data

(63) Continuation of application No. 15/205,651, filed on Jul. 8, 2016, now Pat. No. 9,575,011, which is a
(Continued)

(51) Int. Cl.
*G01N 21/95* (2006.01)
*G06T 7/00* (2017.01)

(52) U.S. Cl.
CPC ....... *G01N 21/9508* (2013.01); *G06T 7/0004* (2013.01)

(58) Field of Classification Search
CPC combination set(s) only.
See application file for complete search history.

(56) References Cited

U.S. PATENT DOCUMENTS

| 4,593,190 A | 6/1986 | Kawasaki et al. |
| 5,392,359 A * | 2/1995 | Futamura ................. A24C 5/34 209/536 |

(Continued)

FOREIGN PATENT DOCUMENTS

| EP | 1112473 | 7/2001 |
| GB | 2252404 | 8/1992 |

(Continued)

OTHER PUBLICATIONS

Rule 71(3) Communication (with text intended for grant) for related EPC patent application No. 11819167.5, mailed by the European Patent Office dated Jul. 1, 2015 (24 pages).

(Continued)

*Primary Examiner* — Janese Duley
(74) *Attorney, Agent, or Firm* — Klarquist Sparkman, LLP

(57) ABSTRACT

An apparatus for acquiring a two-dimensional image of an external surface of a three-dimensional object is described. The apparatus includes a conveyor for supporting and displacing the object, a camera for capturing images of portions of the object surface, and a friction member for rotating the object. The camera is configured to capture images corresponding to successive exposed portions of the object surface, and to sequentially capture the images as respective single frames. The apparatus further includes an electronic control unit adapted to read out a sub-frame from the single frame, store the sub-frame, and assemble successive sub-frames into an assembled frame corresponding to a two-dimensional image of a surface area of the object.

27 Claims, 1 Drawing Sheet

Related U.S. Application Data continuation of application No. 13/878,294, filed as application No. PCT/IB2011/002849 on Oct. 5, 2011, now Pat. No. 9,414,027.

(60) Provisional application No. 61/391,139, filed on Oct. 8, 2010.

(56) References Cited

U.S. PATENT DOCUMENTS

| | | | | |
|---|---|---|---|---|
| 5,437,537 | A * | 8/1995 | Sweet | B65G 57/00 198/456 |
| 5,463,465 | A * | 10/1995 | Yamamoto | G01N 21/9508 209/577 |
| 2008/0047803 | A1 * | 2/2008 | Ackley, Jr. | B65G 47/24 198/406 |
| 2009/0058991 | A1 * | 3/2009 | Kim | G03B 37/04 348/37 |
| 2012/0330665 | A1 * | 12/2012 | Berkun | G06F 19/3462 704/260 |

FOREIGN PATENT DOCUMENTS

| | | |
|---|---|---|
| JP | S62-39746 A | 2/1987 |
| JP | 2002-350358 A | 12/2002 |
| WO | WO 2010/058312 | 5/2010 |

OTHER PUBLICATIONS

International Search Report and Written Opinion for PCT App. No. PCT/IB2011/002849, mailed by the European Patent Office acting as the ISA dated May 7, 2012.

* cited by examiner

APPARATUS AND METHOD FOR ACQUIRING A TWO-DIMENSIONAL IMAGE OF THE SURFACE OF A THREE-DIMENSIONAL OBJECT

CROSS REFERENCE TO RELATED APPLICATIONS

This is a continuation of U.S. application Ser. No. 15/205,651, filed Jul. 8, 2016, which is a continuation of U.S. application Ser. No. 13/878,294, filed Aug. 6, 2013, which is the U.S. National Stage of International Application No. PCT/IB2011/002849, filed Oct. 5, 2011, which was published in English under PCT Article 21(2), which in turn claims the benefit of priority of U.S. Provisional Application No. 61/391,139, filed on Oct. 8, 2010; each of these applications is specifically incorporated by reference herein in its entirety.

FIELD

The invention relates to an apparatus and a method for acquiring a two-dimensional image of the surface of a three-dimensional object.

BACKGROUND

The invention finds particular applications in the pharmaceutical and healthcare fields, especially to perform a quality control process of capsules, caplets, pills and others as three-dimensional objects. In such fields, a two-dimensional image of the external surface may be used to inspect printing, surface condition, shape, colour, dimension or any visible feature, especially to detect the presence of a defect or physical damage. The two-dimensional image may generally be used to reveal any suitable information that can result from an observation of the external surface, such as the length of a capsule. Applications of the invention are, however, not limited to the above mentioned applications in the pharmaceutical and healthcare fields.

The invention is more specifically directed to an apparatus comprising:
displacing means for supporting and displacing the object along a path;
a single camera for capturing images of portions of the object surface;
rotating means for rotating the object about one of its axes along a section of said path, so as to expose successive portions of the object surface to said single camera, whereby the single camera is able to capture images corresponding to successive exposed portions of the object surface.

Such an apparatus is known from EP-A-1 112 473.

SUMMARY

In the apparatus disclosed in this document, the sensing means include a matrix sensor which acquires images of limited portions of the exposed surface of the object on a continuous incremental basis. The limitation of the portions imaged on the matrix sensor is achieved by mechanical means including a moveable mask provided with a slit.

The main problems associated with the apparatus of this type are the complexity of the mechanical system, which is increased by the presence of the movable mask, and the need for intense illumination, due to the presence of the slit which significantly affects the effectiveness of the illumination.

The main objectives of the invention are thus to reduce both the complexity of the mechanical system and the illumination needed for the operation of such an apparatus.

To this end, the invention provides for an apparatus of the aforementioned type, wherein the single camera is configured to sequentially capture the images as respective single frames and the apparatus further comprises electronic processing means adapted, for each successive single frame, to
read out a sub-frame from the single frame, said sub-frame corresponding to a respective individual portion of the exposed portion of the object surface, whereby said successive sub-frames correspond to successive and adjacent individual portions of the object surface with a pre-defined mutual overlap,
store said sub-frames; and
assemble the successive sub-frames into an assembled frame corresponding to a two-dimensional image of an unpeeled surface area of the object.

Hence, the apparatus according to the invention permits to image only a well-defined elementary area of the whole exposed portion of the external surface through an electronic processing of the exposed portion viewed by the imaging device. The system is simplified as it eliminates the need for a physical slit associated with a mobile mechanical component. Beyond the reduction of the manufacturing cost, an increased reliability of the apparatus is obtained with the invention. The elimination of the physical slit, or mask, also allows independent electronically adjustable setting of the size of the sub-frames and the illumination levels.

In addition, the electronic processing permits to improve the adaptability of the apparatus to different objects or dimensions, e.g. to different sizes of capsules, especially thanks to an appropriate choice of sub-frames. With the invention, the number and size of sub-frames can be selected dependent upon the surface geometry of the 3-D object and the desired quality of the assembled image.

As opposed to the above-identified prior art, the apparatus and method according to the invention operate in a discontinuous mode to capture and reassemble discrete subframes to cover the entire object surface.

Optionally, the apparatus according to the invention may include one or more of the following features:
the electronic processing means are adapted to read-out successive sub-frames having no mutual overlap;
the electronic processing means are adapted to define successive sub-frames having a rectangular shape;
the path along which the object is displaced by the displacing means extends in a direction and the axis of rotation of the object defined by the rotating means is substantially perpendicular to said direction;
the single camera has a viewing direction and the path along which the object is displaced by the displacing means extends in a plane substantially perpendicular to the viewing direction; and
the displacing means comprise at least one carrier provided with a housing configured to receive the object and the rotating means comprise a friction member arranged to contact locally the external surface of the object when said object is placed in the housing of the carrier, the displacing means further comprising a driving member adapted to move the carrier relative to the friction member.

In a second aspect, the invention relates to a method of acquiring a two-dimensional image of the external surface of a three-dimensional object comprising:
supporting and displacing the object along a path;
capturing images of portions of the object surface with a single camera;

rotating the object about one of its axes along a section of said path, so as to expose successive portions of the object surface to said single camera, whereby the single camera is able to capture images corresponding to successive exposed portions of the object surface.

According to the invention, the method comprises the steps of sequentially capturing the images as respective single frames and processing the successive single frames by performing the following steps reading out a sub-frame from each single frame, said sub-frame corresponding to a respective individual portion of the exposed portion of the object surface, whereby said successive sub-frames correspond to successive and adjacent individual portions of the object surface with a pre-defined mutual overlap, storing said sub-frames; and assembling the successive sub-frames into an assembled frame corresponding to a two-dimensional image of an unpeeled surface area of the object.

Optionally, the method according to the invention may include one or more of the following features:

the reading out step consists in reading out successive sub-frames having no mutual overlap;

the processing step comprises defining successive sub-frames having a rectangular shape;

the path along which the object is displaced extends in a direction and the axis of rotation of the object is substantially perpendicular to said direction;

the step of capturing images is performed by the single camera oriented in a viewing direction and the path along which the object is displaced extends in a plane substantially perpendicular to the viewing direction; and the step of rotating the object is performed by means of a friction member arranged to contact locally the external surface of the object when said object is displaced relative to the friction member.

In a third aspect, the invention relates to the use of an apparatus or of a method as described above for acquiring a two-dimensional image of the external surface of a capsule of the type used in the pharmaceutical or healthcare fields.

In such application, the assembled frame may be defined by a number of sub-frames which is higher than 10, preferably higher than 20, and most preferably greater than 30.

BRIEF DESCRIPTION OF THE DRAWINGS

Other objects and advantages of the invention will emerge from the following disclosure of a particular embodiment given as non limitative example, the disclosure being made in reference to the enclosed drawings in which.

DETAILED DESCRIPTION

On the Figures, the same reference numbers refer to the same or similar elements.

Figure 1:
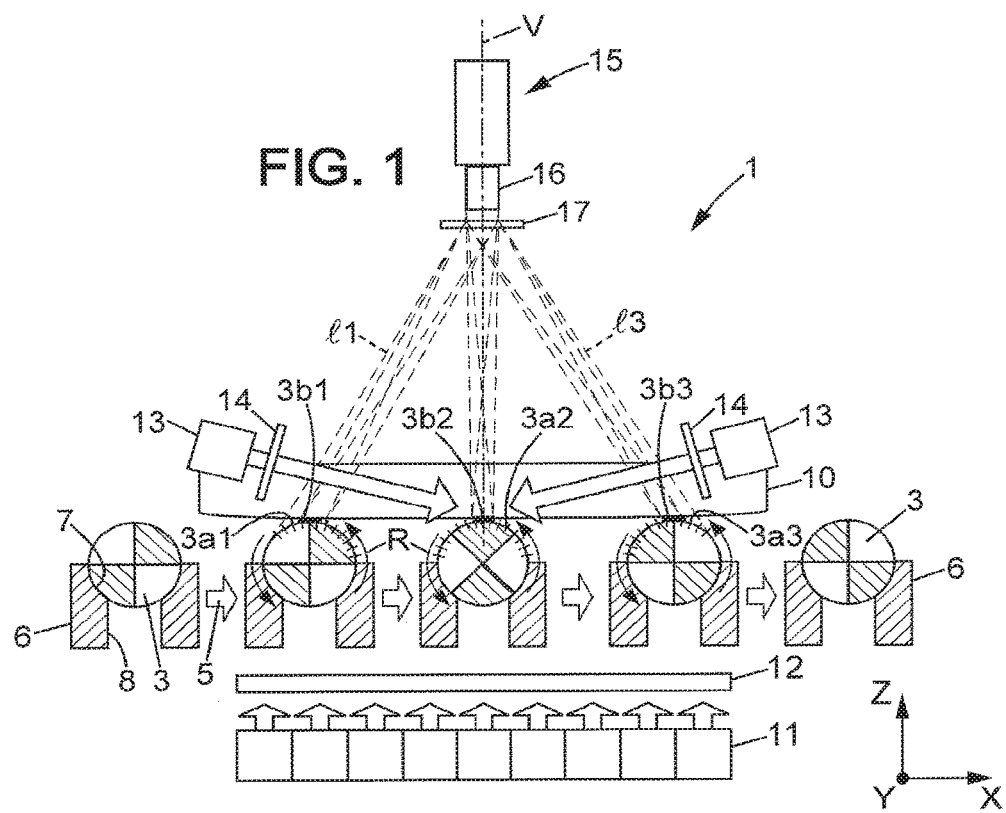
FIG. 1 is a schematic elevation view of an apparatus according to a particular embodiment of the invention.

FIG. 1 illustrates an apparatus 1 for acquiring a two-dimensional image 2 (visible on FIG. 2) of an external surface of capsules, of the type used in the pharmaceutical or healthcare fields.

Of course, the invention is not limited to this particular application and such an apparatus may be used to inspect the external surface of other three-dimensional objects used in the pharmaceutical and healthcare industry, such as caplets, pills or other dosage forms. Beyond these preferred applications, the invention is also applicable to the inspection of other three-dimensional objects in different fields.

The apparatus 1 shown on FIG. 1 is used in a quality control process to detect any defect in the external surface of the capsules 3 conveyed in a production line. The invention allows for a reliable and continuous in-line inspection of each of the capsules. Once a defect, especially regarding the shape, the colour, print characters or others, is detected on the image of the external surface of one of the capsules 3, this capsule 3 is removed from the production line. Also, the apparatus shown on FIG. 1 is used to generate feedback on the manufacturing process.

The illustrated capsules 3 are of the "hard-shell" type, each having a generally cylindrical shape of circular cross-section along a central axis and comprising a container made of two halves telescopically fitted in one another. The container can be empty or filled with an appropriate content, in the appropriate form (powder, liquid or other).

The apparatus 1 comprises displacing means in the form of a linear conveyor 5, schematically represented by straight arrows, driven horizontally in a longitudinal direction X thanks to an appropriate driving member. On FIG. 1, one can consider that only a part of the conveyor 5 is shown. Actually, the represented apparatus 1 could be a station performing the quality control process of a production line, the conveyor 5 being further used to convey the capsules 3 to different stations performing different tasks of the production process.

The conveyor 5 supports a carrier 6 provided with a housing 7 configured to receive the capsule 3. In particular, the housing has a semi-cylindrical shape extending in a transverse direction Y, horizontal and perpendicular to the longitudinal direction X. The housing 7 is sized to accommodate a lower half of the capsule 3. On FIG. 1, the same carrier 6 is shown on different positions occupied as the linear conveyor 5 is driven along the longitudinal direction X. Although represented with only one carrier 6, the conveyor 5 could be provided with a plurality of carriers 6 spaced from each other in an appropriate manner as it will become apparent from the following.

Therefore, as can be seen on FIG. 1, an upper half of the capsule 3 placed in the housing 7 of the carrier 6 presents a free region of external surface directed generally in a vertical direction Z perpendicular to the longitudinal X and transverse Y directions. Depending on the nature and the implementation of the displacing means, the free region of external surface might have any other extent than one half of the external surface and any other location than on the upper half.

The apparatus 1 also comprises rotating means, in the form of a friction bar 10, extending in the longitudinal direction X, arranged at a distance in the vertical direction Z from the carrier 6 and facing the housing 7. The friction bar 10, having preferably a reduced width in the transverse direction Y, is positioned to contact locally a top area of the free region of external surface of the capsule 3 when the capsule is placed in the housing 7 of the carrier 6. The friction bar 10 is made of a material which is adapted, when contacting the external surface of the capsule 3, to produce a frictional effect allowing the capsule 3 to be rotated in the carrier 6. The friction between the capsule 3 and the carrier 6 needs to be less than the friction between the capsule 3 and the bar 10.

The apparatus 1 also comprises an illumination device arranged to illuminate the external surface of the capsule 3. In the illustrated embodiment, the illumination device includes a lower array of light-emitting diode 11 (LED) and two upper arrays of LED 13.

The lower array of LED 11 is arranged in the longitudinal direction X underneath the conveyor 5 to illuminate, where needed through a diffuser 12, a bottom region of the external surface of the capsule 3. In order to allow the illumination of the capsule from the lower side, the carrier 6 is provided with an optical transmissive or diffusive window communicating with the housing 7, in the form of a through-hole 8 in the illustrated embodiment.

The upper arrays of LED 13 are arranged in the transverse direction Y substantially at each end of the friction bar 10, to illuminate the free region of the external surface of the capsule 3, where needed through crossed polarisers 14. In certain cases, the use of cross-polarisers can be avoided by setting appropriate illumination angles.

It should be noted that the illumination could also be configured for only a front light illumination of the object by the upper arrays of LED. In such case, a reflective and/or diffusive element would preferably be provided in the housing 7 so as to obtain an optical reflection and thus allow the colour (or other optical characteristic) to be made apparent.

As the capsule 3, placed in the housing 7 of the carrier 6 with its central axis extending in the transverse direction Y, is moved in the longitudinal direction X by the conveyor 5, its free region of external surface contacts the friction bar 10. This causes the capsule 3 to rotate about its central axis (counter-clockwise in the illustrated embodiment, as shown by circular arrows R). Successive portions of the external surface run on the free region (meaning the exposed region of the capsule, above the carrier) of the external surface, the fiction bar 10 having a length chosen so that the entire external surface of capsule 3 may run successively on the free region.

In the illustrated embodiment, the conveyor 5 and the friction bar 10 define a linear path along which the capsule 3 is moved in translation so as to expose successively a plurality of portions 3a of the external surface on the free region to an imaging device in the form of a camera 15. As it will become apparent from the following, the plurality of exposed portions 3a of the external surface includes the entire external surface of the capsule 3.

The invention is not limited to the above arrangement of the displacing means, rotating means and illuminating device. In particular, the carrier 6 and the friction bar 10 could be arranged in any other appropriate location to provide the rotational movement of the capsule 3. Besides, the moving device could be provided with a driving member adapted to move the friction bar 10 with respect to the carrier 6 rather than the disclosed driving member adapted to move the carrier 6 with respect to the friction bar 10. Moreover, in other embodiments, other suitable moving devices adapted to move the objects along any other kind of path, such as an arcuate path, could be provided.

To scan and image the external surface of the capsule 3, the camera 15 is arranged to view the plurality of exposed portions 3a of the external surface running on the free region. In particular, the camera 15 has a field of view of a rectangular shape. This rectangular shape extends within a cone extending from a lens 16 in a viewing direction V, which is parallel to the vertical direction Z in the illustrated embodiment, and widening towards the friction bar 10 so as to cover the path within which the plurality of portions 3a of the external surface are exposed. The lens 16 of the camera 15 might be equipped with a crossed polariser 17.

As visible on FIG. 1, the external surface which is placed within the field of view of the camera 15 and which faces the camera 15 forms the exposed portion 3a of the external surface. On FIG. 1, three exposed portions 3a1, 3a2 and 3a3, shown with hatched lines, corresponding to three successive positions of the capsule 3 within the path, are represented.

When the capsule 3 is in the first position (second representation of the capsule 3 from the left), the first exposed portion 3a1 which faces the camera 12 does not extend on the whole free region of the external surface since the capsule 3 is offset with respect to the viewing direction V. The first exposed portion 3a1 extends between an imaginary straight dashed line 11 tangential to the external surface of the capsule 3 on the left hand, and the carrier 6 on the right hand.

When the capsule 3 is in the second position (third representation of the capsule 3), the second exposed portion 3a2 which faces the camera 12 extends on the free region of the external surface since the capsule 3 is aligned with respect to the viewing direction V.

When the capsule 3 is in the third position (fourth representation of the capsule 3 from the left), the third exposed portion 3a3 which faces the camera 12 does not extend on the whole free region of the external surface either since the capsule 3 is offset with respect to the viewing direction V. The third exposed portion 3a3 extends between the carrier 6 on the left hand, and an imaginary straight dashed line 13 tangential to the external surface of the capsule 3 on the right hand.

Out of the whole exposed portion 3a of the external surface within the field of view and viewed by the camera 15, the camera 15 is controlled to acquire an image limited to an elementary area 3b of the exposed portion 3a. In the illustrated example, the elementary area 3b is arranged substantially within a horizontal plan flush with the top area of the external surface of the capsule 3.

To that end, the apparatus comprises an electronic control unit (not shown) that is connected to the camera 15 and the conveyor 5 so as to synchronise the acquisition of images performed by the camera 15 with the movement of the capsule 3 performed by the conveyor 5. In addition, the electronic control unit is adapted to limit the image acquisition of the exposed portion 3a of external surface to a subframe 2a, visible on FIG. 2, corresponding to an image of the elementary area 3b of the external surface of the capsule 3. As the capsule 3 travels along the path, the exposed portions 3a of the external surface of the capsule 3 are changed and the camera 15 acquires a number of successive subframes 2a corresponding respectively to images of adjacent elementary areas 3b of the external surface.

For example, on FIG. 1, the elementary areas 3b are shown with a thick line, between two imaginary dashed lines starting from the lens 16 and schematically representing the subframe. When the capsule 3 is in the first position, only the first elementary area 3b1 of the first exposed portion 3a1 is imaged. When the capsule 3 is in the second position, only the second elementary area 3b2 of the second exposed portion 3a2 is imaged. When the capsule 3 is in the third position, only the third elementary area 3b3 of the third exposed portion 3a3 is imaged.

The number and the size of the subframes 2a are chosen so that adjacent elementary areas 3b1 compose the entire external surface of the capsule 3. Therefore, through the acquisition of the successive subframes 2a corresponding respectively to the images of the adjacent elementary areas 3b, the external surface may be unwrapped, the successive subframes 2a being then assembled to form the assembled frame corresponding to the two-dimensional image of the external surface as shown on FIG. 2.

Figure 2:
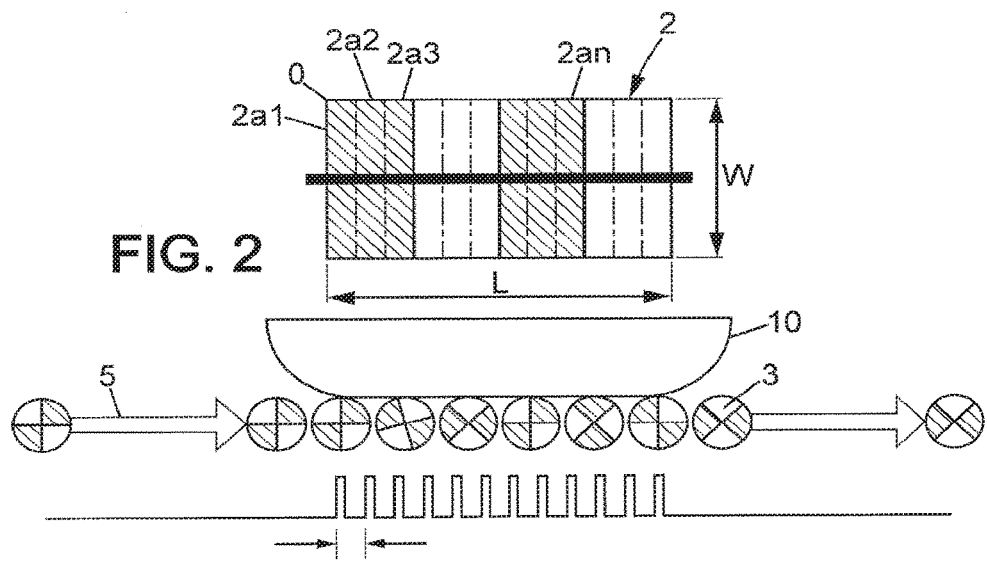
FIG. 2 is a schematic illustration of a method according to the invention, the method being carried out by the apparatus of FIG. 1.

Reference is now made to FIG. 2, which illustrates the synchronisation of the triggering of the acquisition of the subframes with the displacing means, and the assembling of the successive subframes to obtain a two-dimensional image of the external surface.

In the illustrated example, the camera 15 is controlled to acquire twelve successive small, letter-box shaped images of the top areas of the exposed portions 3a of the external surface within the path. The resulting twelve rectangular subframes 2a are then assembled to form the assembled frame on FIG. 2. A part of the top area hidden by the friction bar 10 is not visible on the resulting image. This could be avoided through another arrangement of the friction bar 10.

In relation to FIG. 2, a method for acquiring the two-dimensional image of the external surface of the capsule 3 implementing the above disclosed embodiment of the apparatus 1 is disclosed.

The plurality of portions 3a of the external surface is exposed to the camera 15 thanks to the rotation imparted to the capsule 3 by the conveyor 5 and the friction bar 10, as previously explained.

A number and a size of successive subframes 2a to be acquired within the plurality of exposed portions 3a of the external surface are then determined by the electronic control unit. In particular, the number and the size of the subframes can be preset in a memory of the electronic control unit or programmed through a communication interface.

In the illustrated example, twelve subframes 2a of rectangular shape corresponding to the images of twelve adjacent top areas of the external surface of the capsule 3 as it is advanced along the path are to be acquired. The number of subframes can of course be different and adapted to the size of the capsules or objects to be inspected and as well to the quality of the final image required.

Typically, the number of subframes can be in the range of 6 to 36. Preferably, for example in an application to capsule inspection, this number is higher than 10, preferably higher than 20, and most preferably greater than 30.

Then, the electronic control unit may proceed with the calculation of the coordinates of each of the successive subframes 2a along first and second directions of a reference plane attached to the field of view. In the illustrated embodiment, the reference plane is a horizontal plane flush with the top area of the external surface of the capsule 3. The first direction corresponds to the longitudinal direction X and the second direction corresponds to the transverse direction Y. In this reference plane, the field of view has a dimension in the longitudinal direction X, corresponding to a length L, and a dimension in the transverse direction Y, corresponding to a width W.

The coordinates in the longitudinal direction X of the successive subframes are determined by the electronic control unit by incrementing, from an origin O, an X-coordinate with an offset equal to the ratio of the length L of the field of view to the number of successive subframes in the first direction X. The Y direction is determined by the width of the field of view W.

In the illustrated example wherein the twelve successive subframes have no mutual overlap and extend each along the whole width W of the field of view, the coordinates, in pixel or mm, of each subframe 2a may defined by a couple of points corresponding to opposite edges of the subframe in the following way:

subframe 2a1: (0; 0), (length L/12-1 pixel or mm; width W), subframe 2a2: (length L/12; 0), (2*length L/12-1 pixel or mm; width W), subframe 2a3: (2*length L/12; 0), (3*length L/12-1 pixel or mm; width W),

. . .

subframe 2an: ((n−1)*length L/12; 0), (n*length L/12-1 pixel or mm; width W), with n=1, . . . , 12.

As can be seen on FIG. 2, the acquisition of the successive subframes is synchronised with the movement of the capsule 3 and can be triggered when the centre line of the capsule is in the centre of the subframe. When the conveyor 5 comprises several carriers 6, a pitch between two successive carriers 6 should be calculated on the basis that the complete surface of the object can be imaged.

To obtain the two-dimensional image 2 of the external surface of the capsule 3, the successive subframes 2a1, 2a2, 2a3, . . . , are then assembled by the electronic control unit.

The sequence from optical imaging of the moving capsule to creating a final assembled frame for image processing is as follows:

(i) the sensor of the camera is cleared;
(ii) an optical image of the capsule is projected onto the 2D sensor of the camera;
(iii) the whole image of the capsule in that position is captured on the sensor as a single frame;
(iv) a region of the frame, the subframe of interest, is read-out, transferred and stored;
(v) the subframe is added/inserted into the target assembled frame;
(vi) the capsule continues to move forward exposing a new region to be imaged;
(vii) the process is repeated from step (i) onwards until all the subframes have been imaged and transferred into the assembled frame;
(viii) the final image processing is carried out on the final assembled frame.

The above description has been made in relation to a capsule having a cylindrical shape of circular cross-section along a central axis. The invention is, however, not limited to the acquisition of a two-dimensional image of the cylindrical external surface of such three-dimensional object and could be applied to acquire a three-dimensional object having any other shape, for example with a more complex external surface.

To that end, the moving device can be adapted in any appropriate manner to move, and especially translate and rotate, the object with respect to a larger number of axes than that of the above disclosed embodiment. In particular, the object could be translated and/or rotated with respect to at least two of three orthogonal axes, including a longitudinal axis, a transverse axis and a vertical axis. Besides, the electronic control unit and the camera can be adapted to acquire the appropriate subframes for example through the definition of appropriate shape of the subframes and the calculation of the appropriate coordinates of the subframes.

The invention provides for an apparatus and a method wherein a 3D object surface is imaged and translated into a 2D representation without significant distortion or reduction in image quality based on the use of a single camera and without the use of a mechanical shutter arrangement. The assembled frame is constructed digitally, as opposed to constructed optically, on a single camera sensor frame, from a plurality of subframes. The sizing of the subframes is chosen to ensure that the projection of the 3D object surface into the 2D assembled frame has minimal distortion and degradation.

The translation and rotation of the object can be controlled such that the whole external surface is completely exposed within the assembled frame. In an alternative embodiment, the complete external surface may be under- or over-driven to expand or compress to fit within the assembled frame.

The invention claimed is:

1. An apparatus for acquiring a two-dimensional image of an external surface of a three-dimensional object, comprising:
a conveyor that displaces the object along a path;
a camera for capturing images of portions of the object surface;
a friction member that engages with the object to cause the object to rotate about an axis of rotation to vary the object surface that is exposed to the camera to provide a plurality of exposed portions of the object surface, wherein the camera is configured to capture images corresponding to the exposed portions of the object surface, and wherein the camera is configured to capture the images as respective single frames;
a source of illumination; and
an electronic control unit adapted, for each single frame, to:
read out a sub-frame from the single frame, the sub-frame corresponding to a respective individual portion of the exposed portion of the object surface, whereby the sub-frames correspond to individual portions of the object surface; and
assemble the sub-frames into an assembled frame corresponding to a two-dimensional image of a surface area of the object,
wherein the object is a cylindrical capsule with a circular cross section along a central axis of the type used in pharmaceutical or healthcare applications, the conveyor includes at least one spacing member that spaces the object apart from a second three-dimensional object being displaced by the conveyor and a driving member adapted to move the spacing member relative to the friction member to displace the object along the path,
wherein the friction member is arranged to contact locally the external surface of the object when the object is displaced along the path by the conveyor, and
wherein the friction member has a first side and a second side, and the camera is positioned on the first side of the friction member and the source of illumination is positioned on the second side.

2. The apparatus of claim 1, wherein the individual portions of the object surface have no mutual overlap.

3. The apparatus of claim 1, wherein the individual portions of the object surface mutually overlap.

4. The apparatus of claim 1, wherein the electronic control unit is adapted to define successive sub-frames having a rectangular shape.

5. The apparatus of claim 1, wherein the path along which the object is displaced by the conveyor extends in a direction and the axis of rotation is substantially perpendicular to the direction.

6. The apparatus of claim 1, wherein the camera has a viewing direction and the path along which the object is displaced by the conveyor extends in a plane substantially perpendicular to the viewing direction.

7. The apparatus of claim 1, wherein the assembled frame is defined by at least ten sub-frames.

8. The apparatus of claim 1, wherein the friction member comprises a friction bar that extends along a section of the path.

9. The apparatus of claim 8, wherein the friction bar is positioned between the camera and the capsule.

10. The apparatus of claim 1, wherein respective single frames further comprise images corresponding to an additional exposed portion of at least one additional object being supported and displaced by the conveyor.

11. A method of acquiring a two-dimensional image of the external surface of a three-dimensional object that is a cylindrical capsule with a circular cross section along a central axis of the type used in pharmaceutical or healthcare applications, comprising:
displacing the object along a path of a conveyor;
illuminating the object from below with a source of illumination;
capturing images of portions of the object surface with a camera;
rotating the object about an axes of rotation extending along a section of the path to expose different portions of the object surface to the camera by contacting the external surface of the object with a friction member while the object moves relative to the friction member, wherein the friction member has a first side and a second side, and the camera is positioned on the first side of the friction member and the source of illumination is positioned on the second side;
wherein the camera is configured to capture images corresponding to the exposed portions of the object surface;
capturing the images as respective single frames; and
processing the single frames by
reading out a sub-frame from each single frame, the sub-frame corresponding to a respective individual portion of the exposed portion of the object surface, whereby the sub-frames correspond to individual portions of the object surface; and
assembling the successive sub-frames into an assembled frame corresponding to a two-dimensional image of a surface area of the object.

12. The method of claim 11, wherein the individual portions of the object surface have no mutual overlap.

13. The apparatus of claim 12, wherein the individual portions of the object surface mutually overlap.

14. The method according to claim 11, comprising defining sub-frames that have a rectangular shape.

15. The method of claim 11, wherein the path along which the object is displaced extends in a direction and the axis of rotation is substantially perpendicular to the direction.

16. The method of claim 11, wherein the capturing is performed by the camera oriented in a viewing direction and the path along which the object is displaced extends in a plane substantially perpendicular to the viewing direction.

17. The method of claim 11, wherein the rotating is performed by a friction member arranged to contact locally the external surface of the object when the object is displaced relative to the friction member.

18. The method of claim 17, wherein the friction member comprises a friction bar that extends along a section of the path between the camera and the capsule.

19. The method of claim 11, wherein the respective single frames further comprise images corresponding to an additional exposed portion of at least one additional object being supported and displaced by the conveyor.

20. The apparatus of claim 1, further comprising an illumination device.

21. The apparatus of claim 20, wherein the conveyor comprises a through-hole so that light from an illumination device can pass through the conveyor to illuminate at least a portion of the external surface of the object.

22. The apparatus of claim 9, wherein the friction bar has a reduced width relative to a width of the capsule to reduce an amount of the capsule that cannot be captured by the camera due to the position of the friction bar.

23. The apparatus of claim 1, wherein the source of illumination comprises an array of light-emitting diodes.

24. The apparatus of claim 1, wherein the source of illumination comprises a reflective element that is illuminated by an illumination device.

25. The method of claim 11, wherein the act of illuminating the object from below comprises using an illumination device posited below the object.

26. The method of claim 1, wherein illuminating the object from below comprise reflecting light toward the object from a location below the object.

27. An apparatus for acquiring a two-dimensional image of an external surface of a three-dimensional object, comprising:
 a conveyor that displaces the object along a path;
 a camera for capturing images of portions of the object surface;
 a friction member that engages with the object to cause the object to rotate about an axis of rotation to vary the object surface that is exposed to the camera to provide a plurality of exposed portions of the object surface, wherein the camera is configured to capture images corresponding to the exposed portions of the object surface, and wherein the camera is configured to capture the images as respective single frames; and
 an electronic control unit adapted, for each single frame, to:
 read out a sub-frame from the single frame, the sub-frame corresponding to a respective individual portion of the exposed portion of the object surface, whereby the sub-frames correspond to individual portions of the object surface; and
 assemble the sub-frames into an assembled frame corresponding to a two-dimensional image of a surface area of the object, the assembled frame being defined by at least ten sub-frames,
 wherein the object is a cylindrical capsule with a circular cross section along a central axis of the type used in pharmaceutical or healthcare applications, the conveyor includes at least one spacing member that spaces the object apart from a second three-dimensional object being displaced by the conveyor and a driving member adapted to move the spacing member relative to the friction member to displace the object along the path, and
 wherein the friction member is arranged to contact locally the external surface of the object when the object is displaced along the path by the conveyor.

* * * * *